United States Patent [19]

Bartlett et al.

[11] 4,131,741

[45] Dec. 26, 1978

[54] COBALT-CATALYZED OXIDATION OF $C_3$ TO $C_7$ SATURATED ALIPHATIC HYDROCARBONS TO OXYGENATED PRODUCTS

[75] Inventors: John S. Bartlett, Hull; Barry Hudson, Beverley, both of England

[73] Assignee: BP Chemicals Limited, London, England

[21] Appl. No.: 755,148

[22] Filed: Dec. 29, 1976

Related U.S. Application Data

[62] Division of Ser. No. 706,197, Jul. 16, 1976, Pat. No. 4,086,267.

[30] Foreign Application Priority Data

Jul. 21, 1975 [GB] United Kingdom ............... 30389/75
Sep. 17, 1975 [GB] United Kingdom ............... 38180/75

[51] Int. Cl.² .................... C07C 45/02; C07C 51/20; C07C 67/00
[52] U.S. Cl. .................................... 560/241; 203/71; 203/99; 203/DIG. 11; 260/597 R; 560/248; 568/910; 562/549
[58] Field of Search .................... 260/533 R, 597 R; 560/241

[56] References Cited

U.S. PATENT DOCUMENTS 3,923,882  12/1975  Kiff .................................. 260/533 R
4,032,570   6/1977  Schulz et al. ..................... 260/533 R Primary Examiner—Vivian Garner
Attorney, Agent, or Firm—Brooks, Haidt, Haffner & Delahunty

[57] ABSTRACT

In a process for the production of oxygenated organic compounds including a substantial proportion of acetic acid by oxidizing a $C_3$ to $C_7$ saturated aliphatic hydrocarbon in the liquid phase with molecular oxygen in the presence of an inert reaction medium and a cobalt catalyst, between 5 and 90% in a continuous reaction and 11 and 90% in a batch reaction of the cobalt being introduced in the +3 oxidation state, the improvement comprising separating the catalyst solution fraction from the fraction comprising oxygen-containing compounds and water by distillation while limiting the residence time of the catalyst solution fraction in the distillation zone so that it is the minimum consistent with substantially complete separation of the fractions thereby minimizing the reduction of $Co^{+3}$ to $Co^{+2}$.

10 Claims, 3 Drawing Figures

COBALT-CATALYZED OXIDATION OF $C_3$ TO $C_7$ SATURATED ALIPHATIC HYDROCARBONS TO OXYGENATED PRODUCTS

This application is a division of application Ser. No. 706,197 filed July 19, 1976, now U.S. Pat. No. 4,086,267.

The present invention relates to a process for the liquid phase oxidation of saturated aliphatic hydrocarbons containing 3 to 7 carbon atoms to produce oxygen-containing organic compounds including a substantial proportion of acetic acid, and in particular to a continuous process for the oxidation of butane to acetic acid wherein the catalyst solution is continuously recycled.

Processes for the low-temperature cobalt-catalysed oxidation of lower aliphatic hydrocarbons containing less than 6 carbon atoms are known from British Patent Specification Nos. 709,674 and 1,266,678. Thus British Patent Specification No. 1,266,678 describes and claims a process for converting butane to a product predominating in acetic acid, comprising, at a temperature within the range 66 to 177° C, contacting butane with a gas containing molecular oxygen, in the presence of an inert reaction medium and of a catalyst consisting of a cobalt compound soluble in the reaction medium, the cobalt compound being present in an amount, calculated as cobalt, within the range from 0.4 to 25 percent by weight based on the reaction medium. It is disclosed that the cobalt catalyst may be in the form of a cobaltous or cobaltic compound and indeed all the Examples illustrate the use of the more common cobaltous compound in the form of cobaltous acetate, $Co(OAc)_2.4H_2O$. No distinction is drawn between the use of soluble cobaltous compounds and soluble cobaltic compounds. Whilst it is further stated that the reaction may be effected without a co-oxidant being present, it is clear from Examples 12 and 13 that in order to avoid a long induction period of the order of 42 hours, even in the presence of pure oxygen as oxidant, it is necessary to add a co-oxidant such as methyl ethyl ketone which, while being itself a commercially desirable product of the reaction, adds to the cost of the process.

Furthermore U.S. Pat. No. 3,923,882 discusses the role of promoters in the liquid phase process for the production of acetic acid by the oxidation of low molecular weight hydrocarbons. After discussing the attendant disadvantages associated with a number of hitherto used promoters the conclusion is reached that "the promoter of choice, therefore, became MEK even though a considerable quantity is converted to acetic acid during the reaction with poor efficiency. Since MEK is more expensive than acetic acid, it is a costly choice." The description continues "An even more serious drawback to the use of MEK as a promoter, however, is that, even though the oxidation proceeds very well on a batch scale when all of the reactants are charged to a vessel and nothing is removed until after the completion of the reaction, the same is not true for a continuous operation. When a reaction is started in apparatus to which reactants are continuously added and from which products are removed at about the same rate, the reaction cannot be sustained for more than a few hours. This is true even though cobalt catalyst and MEK are added in sufficient quantities to maintain their concentration at levels which function well for batch oxidations. Since the batch-type operation is too expensive for commercial productions on a large scale, the MEK promoted process is just not feasible." The Examples show that reaction can only be maintained for about 4 hours using MEK as promoter and, except for 2-heptanone and 3-heptanone which are about as effective as MEK, a range of other promoters either result in no reaction or a slow reaction rate. However using ethanol as promoter, continuous reaction was maintained for 18 hours without any indication of the reaction ceasing. The prior art therefore is inconsistent on the choice of a promoter for the reaction, although it would appear that there is a general acknowledgement that a promoter is necessary both to reduce otherwise lengthy induction periods in batch operation and to maintain a continuous process.

We have now found that the induction period can be substantially eliminated during batch operation with or without catalyst recycle and continuous operation maintained without the addition or recycle of a promoter when not less than 5 and not more than 90 percent of the cobalt is introduced in the +3 oxidation state. Additionally when MEK, produced by the oxidation and separated from the products thereof, is recycled to the oxidation reaction higher oxidation rates result.

Thus according to the present invention there is provided a process for the production of oxygen-containing organic compounds including a substantial proportion of acetic acid by the oxidation of a saturated aliphatic hydrocarbon containing from 3 to 7 carbon atoms or a mixture thereof which process comprises contacting the hydrocarbon or mixture thereof in a reaction zone with a molecular oxygen-containing gas in the presence of an essentially inert reaction medium and a soluble cobalt catalyst in an amount, calculated as cobalt, within the range from 0.1 to 10% by weight, based on the weight of reaction medium, at a temperature in the range 70 to 150° C and a pressure sufficient to maintain the reactants in the liquid phase, not less than 5 and not more than 90 percent of the cobalt catalyst being introduced into the reaction zone in the +3 oxidation state in a continuous process and not less than 11 and not more than 90 percent of the cobalt catalyst being introduced into the reaction zone in the +3 oxidation state in a batch process.

Preferably the percentage of cobalt in the +3 oxidation state is in the range 11 to 80 for a batch process and 5 to 50 for a continuous process.

Whilst any saturated aliphatic hydrocarbon containing 3 to 7 carbon atoms or mixtures thereof may be employed in the process of the present invention the preferred hydrocarbon is butane. The butane is preferably used in the form of n-butane but may contain isobutane and minor amounts of other saturated hydrocarbons. Although isobutane may be present in greater proportions it is preferred that the n-butane contain not more than 40% w/w isobutane.

The molecular oxygen-containing gas may be substantially pure oxygen or may be any gas mixture containing molecular oxygen, but is preferably air. Air is preferred as oxidant because the likelihood of forming explosive mixtures in the unreacted gases either at the top of the reactor or in the overhead gas withdrawal system can be prevented far more easily than when using substantially pure oxygen or gas mixtures containing higher concentrations of oxygen than air. Alternatively substantially pure oxygen may be introduced into the reaction mixture together with recycled (or recirculated) off-gases from the oxidation process as a means of reducing the likelihood of forming explosive mixtures in the unreacted gases.

The essentially inert reaction medium may be any inert material in which the cobalt catalyst is soluble, but is preferably a lower fatty acid having from two to four carbon atoms, such as acetic acid, propionic acid and normal butyric acid. When butane is the saturated aliphatic hydrocarbon, it is preferred to employ acetic acid, since it is the desired product, and complicated and unnecessary separation procedures are thereby avoided. Other inert reaction media such as benzene, chlorobenzene, phenyl benzoate or benzoic acid may be used. The amount of inert reaction medium employed is not critical provided that a substantially homogeneous reaction medium is maintained throughout the reaction. The weight ratio of inert reaction medium to saturated aliphatic hydrocarbon may be in the range 1:10 to 100:1.

The amount of soluble cobalt catalyst calculated as cobalt is preferably in the range from 0.2 to 5% by weight. The cobalt catalyst containing cobalt partially in the +3 oxidation state may be prepared from the corresponding compound of cobalt in the +2 oxidation state by any means known in the art. Some such suitable means are by co-oxidation in the presence of acetaldehyde, paraldehyde or methylethyl ketone, by treatment with ozone, or by electrochemical oxidation. Compounds of cobalt in the +2 oxidation state suitable for oxidation to the corresponding compound of cobalt in the +3 oxidation state include cobaltous chloride, sulphate, nitrate, acetate, propionate, butyrate, isovalerate, benzoate, toluate, terephthalate, naphthenate, salicylate, phthalocyanine or acetylacetonate, of which cobaltous acetate is preferred. The cobaltous compound may have been recovered from an earlier oxidation reaction product. The necessary amount of cobalt in the +3 oxidation state in the catalyst may be achieved by partial oxidation of the corresponding compound of cobalt in the +2 oxidation state or simply by mixing a compound of cobalt in the +2 oxidation state with a compound of cobalt in the +3 oxidation state in the desired proportions.

The reaction temperature is preferably in the range 90 to 140° C and a reaction pressure in the range 10 to 100 bar absolute is usually found to maintain the reactants in the liquid phase. Reaction time is not critical being dependent merely upon the extent of conversion required. Thus the reaction period may be in the range of from one minute to 20 hours, preferably from 10 minutes to 3 hours.

The oxygenated products resulting from the oxidation of $C_3$ to $C_7$ saturated aliphatic hydrocarbons comprise carboxylic acids in substantial proportions and minor proportions of ketones, esters and oxides of carbon e.g. carbon monoxide and carbon dioxide. Thus the oxidation of n-butane results in a product comprising predominantly acetic acid, together with minor amounts of propionic acid and butyric acid, methyl ethyl ketone, sec-butyl acetate, ethyl acetate, methyl acetate, acetone, succinic acid, carbon monoxide, carbon dioxide and higher boiling products. Compared with other hydrocarbon oxidation routes to acetic acid, in the oxidation of butane by the process of the present invention the quantity of carbon monoxide, being less than 2% of the acetic acid made, is exceptionally low.

When the process is operated batchwise, the $C_3$ to $C_7$ saturated hydrocarbon, the inert reacton medium and the cobalt catalyst, for example n-butane, acetic acid and Co(+2)/Co(+3) catalyst such as cobaltous/cobaltic acetate respectively may be placed in a closed reactor which is pressurised to the desired reaction pressure with a molecular oxygen-containing gas e.g. air. The temperature of the mixture may then be raised to the desired reaction temperature accompanied by stirring. Since oxygen is consumed in the reaction additional molecular oxygen-containing gas e.g. air may be introduced into the reactor. The reaction may be discontinued at any time but preferably when no further oxygen absorption occurs. The reaction mixture may be brought to atmospheric pressure, withdrawn from the reaction zone and separated into its components.

Alternatively, saturated aliphatic hydrocarbon and molecular oxygen-containing gas may be fed continuously to a reactor containing a cobalt catalyst and inert reaction medium and the oxygenated organic products removed from the reactor, either partially or entirely, by continuously withdrawing substantially liquid-free gases from the top of the reactor, partially cooling said gases thereby providing a condensate which comprises a hydrocarbon-rich phase and an aqueous phase rich in acetic acid, separating the phases and thereafter recycling the hydrocarbon-rich phase to the reactor and separating the aqueous phase into its components. In this manner, as an additional benefit water is continuously withdrawn from the reaction because the ratio of water to acetic acid in the condensate from the reactor off-gas is higher than the corresponding ratio in the reaction mixture by virtue of the fact that the relative volatility of water to acetic acid is greater than unity. The withdrawal of the aqueous acetic acid-rich phase of the overhead condensate therefore leads to a lower standing concentration of water in the reaction mixture and results in a higher reaction rate and a reduced tendency for the reaction mixture to partition into two phases.

It may be advantageous with the above mode of operation to treat the condensate resulting from partially cooling the substantially liquid-free gases withdrawn from the top of the reactor with a metal salt having a high solubility in both water and acetic acid. A preferred metal salt is an alkali metal salt of a carboxylic acid. A particularly preferred metal salt is potassium acetate. It is preferred to treat the condensate with a concentrated solution of the metal salt in a suitable solvent. Suitable solvents are acetic acid, water or mixtures thereof. The salt dissolves preferentially in the aqueous phase rich in acetic acid and thereby aids phase separation and reduces the quantities of water and acetic acid in the hydrocarbon-rich phase, both of which are desirable objectives. The products may be removed from the concentrated metal salt solution in a single distillation or flash evaporation step and the salt solution recycled to the condensate treatment.

Alternatively, or in addition substantially gas-free liquid may be withdrawn from the base of the reactor and separated into residual hydrocarbon, a fraction containing the bulk of the oxygenated organic products and a fraction comprising inert reaction medium with the cobalt catalyst dissolved therein. Preferably the substantially gas-free liquid is separated into a fraction containing the bulk of the reaction products and a fraction comprising the inert reaction medium with the cobalt catalyst dissolved therein by distillation.

Although the process of the invention is applicable to processes in which the catalyst solution is used on a once-through basis, i.e., it is discarded after separation from the oxidation products, it is particularly applicable to oxidation processes in which the fraction comprising inert reaction medium with the cobalt catalyst dissolved therein after separation from the oxidation products, is recycled to the oxidation zone. Thus in a batch process the catalyst solution separated from the oxidation products may be re-used in a further batch operation and in a continuously operated process the separated catalyst solution may be continuously recycled to the oxidation zone.

It has been found that certain of the products resulting from the oxidation of $C_3$ to $C_7$ saturated aliphatic hydrocarbons are capable of reducing cobalt in the $+3$ oxidation state to cobalt in the $+2$ oxidation state. The reduction occurs particularly rapidly under the conditions of elevated temperature prevailing during its separation by distillation and unless measures are taken to maintain the proportion of the cobalt catalyst in the $+3$ oxidation state in the recycle stream to the oxidation zone within the range 11 to 90% for initiation of a batch reaction and 5 to 90, preferably 5 to 50% for a continuous process long induction periods may occur in the case of a batch reaction and in the case of a continuous reaction the oxidation rate may progressively decrease to a point where reaction ceases. Furthermore, it has been noted that when the cobalt catalyst solution is recovered from the reaction products with substantially all the cobalt in the $+2$ oxidation state, partial deposition as insoluble Co $(+2)$ compounds occurs, leading to rapid fouling of heat-exchanger surfaces and frequent blockages in pipes, pumps etc. used for re-introducing the catalysts into the reaction zone, whereas when the catalyst recycle stream contains $Co(+3)$ in the proportions according to the invention, the problem of solids deposition is very much reduced, thereby contributing to the extended operability of the continuous oxidation process.

It is therefore preferred to separate the cobalt catalyst as a solution in inert reaction medium from the water and oxygen-containing organic compounds with which it is mixed by feeding the mixture to a distillation zone wherein a catalyst solution fraction comprising inert reaction medium and cobalt of which from 5 to 90% is in the $+3$ oxidation state for recycle in a continuous process and 11 to 90% is in the $+3$ oxidation state for recycle to a batch process is separated as a base product from a distillate fraction comprising oxygen-containing organic compounds and water, the residence time of the catalyst solution in the distillation zone being so adjusted that it is the minimum consistent with substantially complete separation of the fractions.

The rate of chemical reduction of cobalt in the $+3$ oxidation state to cobalt in the $+2$ oxidation state is directly dependent on the temperature and as a consequence it follows that the shorter the time for which the cobalt catalyst is exposed to the elevated temperature required to separate the reaction products from the catalyst-containing inert reaction medium the less will be the reduction of the cobalt $(+3)$ component of the catalyst to the $Co(+2)$ component.

The residence time of the catalyst solution in the distillation zone are suitably less than 20 minutes, preferably less than 10 minutes when the separation of the fractions is carried out by distillation at atmospheric pressure.

Residence times consistent with substantially complete separation of the fractions may be achieved by employing as the distillation zone either (a) a packed column having as a reboiler a falling film evaporator, or (b) a shallow tray column e.g. of the type used for vacuum distillations in combination with a falling film evaporator or (c) a packed column equipped with a reboiler having a volume sufficiently low to limit the residence time or (d) a shallow tray column in combination with a reboiler of the type described in (c).

In addition the temperature required to separate the catalyst solution fraction from the distillate fraction may be reduced by maintaining the distillation zone under reduced pressure.

The recovered fraction comprising inert reaction medium and cobalt in the $+3$ oxidation state may contain in addition minor amounts of "heavy ends." Because of their higher boiling point the "heavy ends" may tend to build up in the catalyst solution recycle stream. For this reason it may be desirable to remove the heavy ends by cooling all or part of the catalyst solution recycle stream and subjecting it to settling and/or filtration prior to recycle to the reaction oxidation zone.

Whether the reaction products be removed from the reactor by continuously withdrawing substantially liquid-free gases from the top of the reactor or withdrawing a substantially gas-free liquid from the base of the reactor or by a combination of both methods the crude catalyst-free product collected comprises acetic acid, water, minor amounts of other carboxylic acids e.g. propionic acid and butyric acids, methyl ethyl ketone, sec-butyl acetate and trace amounts of alcohols and other volatile ketones and esters, the actual composition depending very much on the composition of the feedstock.

The crude product may be separated by feeding the product to a distillation column wherein a fraction comprising water, methyl ethyl ketone, sec-butyl acetate and minor amounts of alcohols and other volatile ketones and esters, which products, not including water, are collectively hereinafter referred to as "light ends", is taken off as an overhead fraction and condensed thereby forming a water-rich phase and a ketone/ester-rich phase, said water-rich phase being separated and returned wholly or partially to the column at a point near the top thereof and the ketone/ester-rich phase being removed, and passing the base product comprising acetic acid, water and carboxylic acid impurities to a second distillation column wherein water is removed overhead as an azeotrope leaving a base product comprising substantially anhydrous carboxylic acids. By passing the base product to a third distillation column acetic acid may be separated overhead from the other high-boiling carboxylic acids as a substantially pure product. The ketone/ester-rich phase removed from the first column may be further separated into substantially pure methyl ethyl ketone and sec-butyl acetate products if so-desired or may be recycled to the reactor, though their presence in the reactor is not necessary to initiate the oxidation reaction.

Alternatively the condensate from the first distillation column may be separated into a water-rich phase and a ketone/ester rich phase, the water-rich phase being withdrawn and the ketone/ester rich phase being returned at least in part to the column and a base product comprising substantially anhydrous acetic acid and minor amounts of other higher-boiling carboxylic acids passed to a second distillation column wherein substantially pure acetic acid is separated from higher-boiling carboxylic acids. Any ketone/ester-rich phase removed from the first distillation column may be separated to isolate methyl ethyl ketone and sec-butyl acetate or may be returned directly to the reactor.

The invention will now be illustrated with reference to the following Examples in which the apparatus illustrated in the accompanying Drawings was used.

Figure 1:
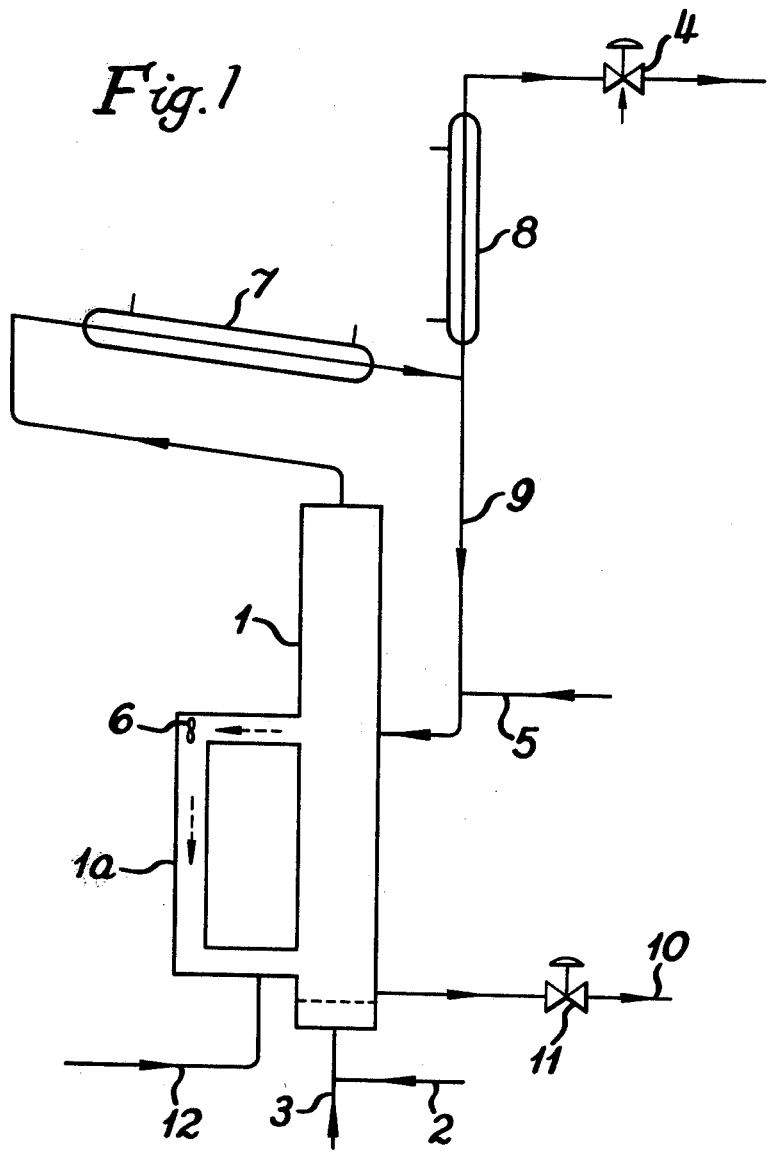
FIG. 1 illustrates a reactor employed in the performance of the invention.

With reference to FIG. 1 the numeral 1 denotes a reaction vessel fabricated in titanium of approximately 5cm. inner diameter and 1m in height having an external pipe loop 1a between the midpoint and the base; 2 is a catalyst inlet pipe; 3 is a gas inlet pipe; 4 is a reactor pressure-controlled gas release valve; 5 is a butane inlet pipe; 6 is a centrifugal liquid-circulation impeller; 7 is a water-cooled condenser; 8 is a refrigerated brine-cooled condenser; 9 is a condensate return pipe; 10 is a reaction mixture take-off pipe; 11 is a reactor level controlled liquid release valve and 12 is a catalyst recycle input pipe.

Figure 2:
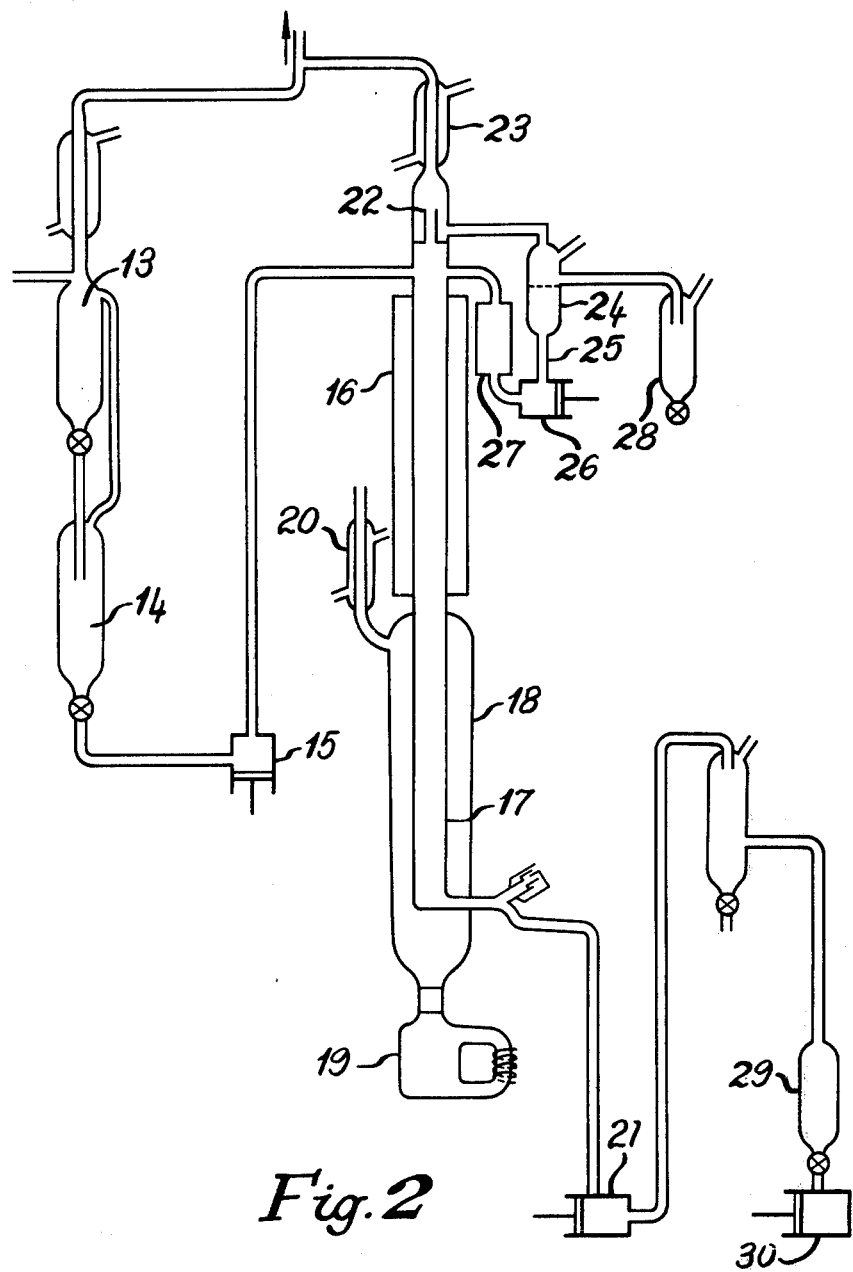
FIG. 2 illustrates a distillation apparatus used for separating the reaction products from the cobalt (+3) catalyst-containing inert reaction medium.

With reference to FIG. 2, 13 denotes a vessel for receipt of reaction mixture from the reactor through line 6 of FIG. 1; 14 is the distillation column feed vessel; 15 is a distillation column feed pump; 16 is a thermally insulated glass column of approximately 2.5 cm inner diameter and 80 cm. in height packed with Raschig rings (6 mm) connecting through a cone and socket joint (not shown) with a falling film evaporator 17, serving as a reboiler, consisting of a glass tube of approximately 2.5 cm inner diameter and 40 cm. in height. A vapour jacket 18 surrounds the evaporator/reboiler 17, the vapour jacket being fed with propionic acid vapour from a reboiler 19 which is condensed in the condenser 20; a pump 21 controls the withdrawal of the catalyst-containing inert reaction mixture base product from evaporator/reboiler 17 which in turn controls the level of the solution within the reboiler and hence to some extent, the rate of vapour generation; 22 is a weir built into the column 16 below the level of a condenser 23; 24 is an overflow vessel from which a line 25 in the base feeds a column reflux pump 26; 27 is a reflux preheater (2-pentanol B.Pt. 119° C); 28 is a pot for receipt of distillate from the overflow vessel 27; 29 is a catalyst feed pot and 30 a catalyst recycle pump.

Figure 3:
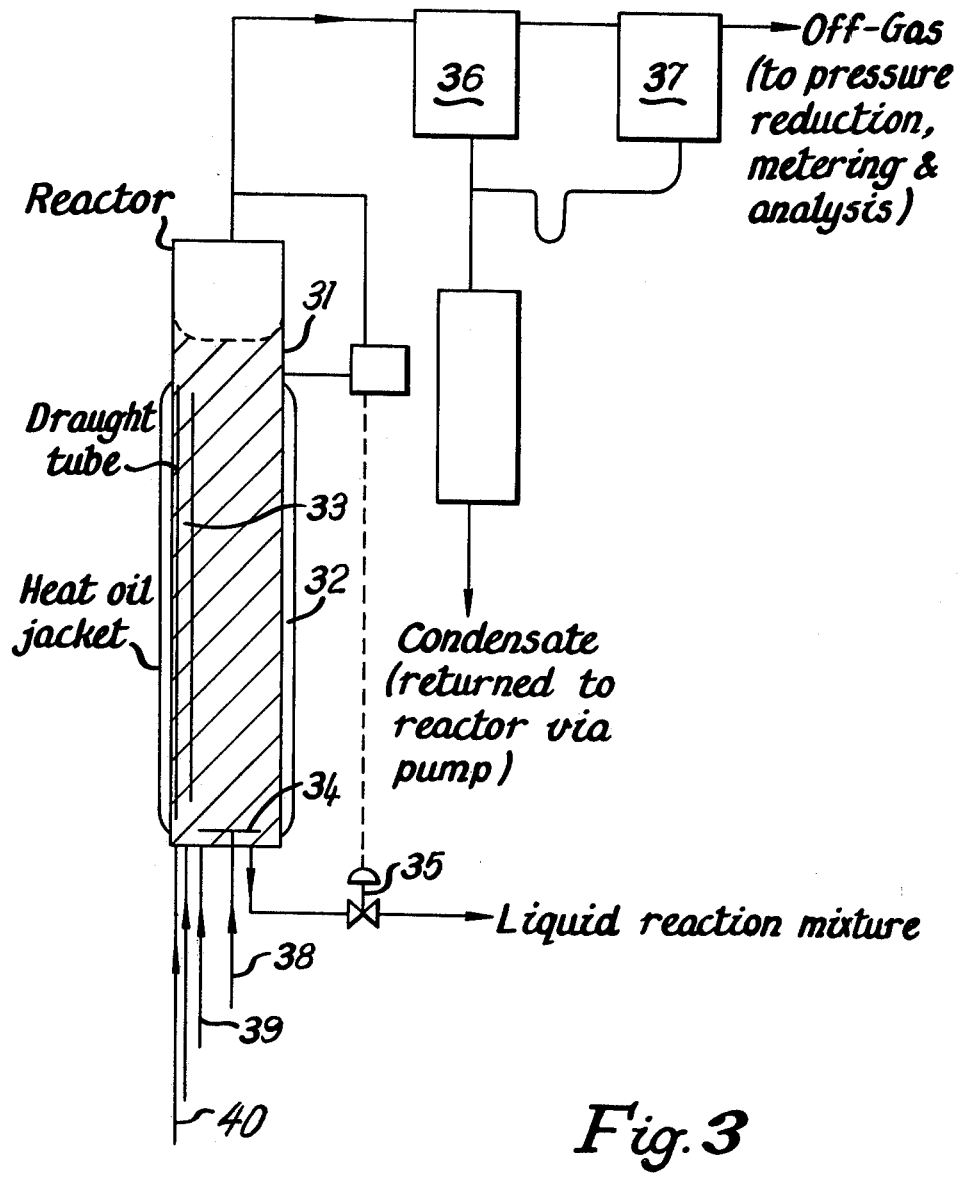
FIG. 3 illustrates another type of reactor employed in the performance of the invention.

With reference to FIG. 3, 31 is a reaction vessel, fabricated in titanium, approximately 1.5 m in height and 10cm. inner diameter. 32 is a heating oil jacket; 33 is a 'draught' tube of segmental cross-section, its purpose being to promote circulation of the reactor contents; 34 is an air distributor; 35 is a level-controlled liquid release valve; 36 is a water-cooled condenser; 37 is a refrigerated brine-cooled condenser; 38 is an air inlet pipe; 39 is a butane inlet pipe; 40 is a condensate return pipe and 41 is a catalyst inlet pipe also functioning as a "light ends" return pipe when operating under "light ends" recycle conditions.

EXAMPLE A

Preparation of catalyst solution

Approximately 5l of acetic acid was charged to a glass vessel equipped with a gas inlet pipe and stirrer. Cobaltous acetate was dissolved in the acetic acid to provide a solution containing about 1% cobalt by weight. Oxygen at a rate of about 7l/h was passed via an OZONO (Registered Trade Mark) air conditioning unit into the stirred vessel at ambient temperature for at least 6 h, thereby converting at least 80% of the cobalt acetate in the solution into the Co(+3) oxidation state. Ozone in the effluent gas was destroyed by passed through vessels containing an aqueous solution of potassium iodide. This is not an Example according to the invention.

EXAMPLE 1

Start-up for continuous operation

With reference to FIG. 1 approximately 1.3l of catalyst solution was introduced into the reaction vessel 1 via pipe 2. A stream of nitrogen was introduced slowly via pipe 3 and the pressure within the reaction vessel was allowed to increase to ca 35 bar absolute by means of the control system which regulated the gas release valve 4. About 250g butane was pumped rapidly into the reactor via pipe 5. About 350l/h, as measured at S.T.P., of air was then introduced via pipe 3 and the reactor heated rapidly to about 110° C by means of external electrical heating elements. The reactor was stirred by the circulation of the liquid contents aided by the centrifugal liquid-circulation impeller 6. Condensation of volatile materials issuing from the top of the reactor was achieved by the water-cooled condenser 7 supplemented by the refrigerated brine-cooled condenser 8, the condensate being returned to the reactor through line 9. Butane was introduced at about 20g/h to compensate for uncondensed butane lost in the off-gases.

By monitoring the oxygen content of the off-gases it was evident that significant oxygen absorption commenced within 15 minutes of the attainment of reaction temperature. The butane feed-rate was then increased to about 100g/h and the withdrawal of liquid reaction mixture, containing reaction products, through pipe line 10 via the reactor level controlled liquid release valve 11 was commenced at this time. Within 1 hour the oxygen content of the off-gases had become reasonably stable at 8 to 9% by volume.

Continuous operation with "light ends" recycle

With reference to FIG. 2 liquid reaction mixture was continuously withdrawn from the reactor via pipe 6 into the reactor product pot 13 held at or near atmospheric pressure, from which the greater part of the butane present in the mixture was removed as gas. The remaining liquid product (approximately 300g/h) was fed through a feed vessel 14 and the feed pump 15 to the top of column 16 where it was heated by vapours passing up the column and thereby itself separated into a vapour and liquid, the liquid passing quickly down the column into the falling-film evaporator 17 wherein both separation and passage downwards of the liquid portion were accelerated. Withdrawal of the catalyst-rich base product was controlled by the pump 21. The distillate passing up the column was condensed by the condenser 23, the condensate falling into the weir 22, from where it flowed into the overflow vessel 24, the overflow passing into the head pot 28 and the remainder being recycled through the line 25, the pump 26 and the preheater 27 to a point in column 16 approximately 10 cm. below the feedpoint, thereby providing the required level of reflux with an additional heat load on the reboiler 19.

The recovered catalyst solution, which contained approximately 1% by weight of cobalt, of which about 30% was in the +3 oxidation state was returned to the reactor 1 via pipe 12 (FIG. 1).

"Light ends" were separated from the reaction products by distillation in a column of approximately 2.5 cm. inner diameter and 140 cm. in height, packed with 6 mm Raschig rings. The feed mixture was introduced near to the midpoint of the column. The distillate separated into two phases and the whole of the lower (aqueous) phase was returned to the top of the column, while the upper (ketone/ester) phase was withdrawn. The base product, withdrawn from the reboiler under liquid level control, comprised essentially all the carboxylic acids and the greater part of the water, with no ketones or esters detectable by gas-liquid chromatography. The ketone/ester phase withdrawn comprised the "light ends" of composition given in Table 1 and additionally contained about 6% water in solution.

The results obtained over a period of about 80 hours of continuous stable operation are presented in Table 1.

The "heavy ends" referred to in the Table are involatile products of the oxidation of butane and comprise mainly succinic acid. This material accumulated in the reaction mixture and recycled catalyst solution, but the net make was subsequently eliminated by partially cooling the catalyst solution followed by setting and/or filtration. Suprisingly little or no loss of cobalt catalyst resulted from this treatment.

EXAMPLE 2

Continuous operation with "light ends" withdrawal

Example 1 was repeated except that the net reaction products, including the "light ends" were withdrawn from the system for separation and analysis.

The results, obtained over a period of 48h continuous operation, are given in Table 1.

It will be seen that the rate of oxygen consumption was about 10% lower than when "light ends" were recycled to the reactor.

The composition of the feed to the short residence time distillation column and the base product recovered therefrom is given in Table 2.

The results presented in Table 2 indicate that the desired rate of removal of acetic acid, "light ends" and a considerable proportion of the water from the catalyst solution was effected. At the same time, a significant proportion of the cobalt was maintained in the +3 oxidation state.

EXAMPLE 3

Using the apparatus illustrated in FIG. 3 the reaction vessel 31 was charged with 8 liters of glacial acetic acid and was pressurised to about 35 bar (absolute). A small nitrogen flow was then established through the pipe 38. Approximately 1 kg. of butane was charged rapidly to the reactor through the line 39 and the butane feed rate was then adjusted to ca. 0.6 kg/h. The oil-heating system was switched on, and a cobalt catalyst solution, comprising 2.2% w/v cobalt, 68% as Co(+3), in acetic acid containing ca. 4% w/w water, was introduced through line 40 at a rate of ca. 1.2 l/h.

When the reactor temperature reached 60° C air was substituted for the nitrogen stream. The oxidation reaction commenced within 15 minutes of attaining a reaction temperature of 120° C. The reaction temperature was stabilised at 125° C and the air and butane feed rates were adjusted to provide an oxygen content in the off-gas of ca. 4% v/v and a (net) acetic acid production rate or approximately 450 g/h.

Liquid reaction mixture withdrawn from the reactor through the valve 35 was passed to a distillation column (approximately 3.5 mm in diameter and 1.8 m in height, packed with 6 mm ceramic Raschig rings), fitted with a specially designed low residence time reboiler fabricated in titanium, to provide a recovered catalyst solution containing cobalt, from 5 to 90% of which was in the +3 oxidation state. Recycle of this catalyst solution through line 40 commenced approximately 3 hours after startup.

"Light ends" were separated from the reaction products in a 20-plate Oldershaw column of approximately 50 mm diameter in a manner similar to that described in Example 1. The "light ends" were thereafter recycled to the reaction vessel.

The continuous oxidation process was operated for a period of approximately 16 days with occasional interruptions, during which period no significant interruption of the oxidation reaction occurred over about 7 consecutive days. During the period of operation reaction conditions were varied to investigate the effects of individual reaction parameters. Results obtained over 8 hours towards the end of this period are given in Table 3.

EXAMPLE B

Example 3 was repeated except that the low-residence time reboiler referred to therein was replaced by a conventional (glass) reboiler of large capacity which led to the recovery of cobalt catalyst solution containing less than 5% of the cobalt in the +3 oxidation state. The formation of cobalt-containing deposits ensued, necessitating frequent interruption of catalyst recycle to clear the various items of equipment. If oxidation ceased (during which time nitrogen was introduced into the reactor off-gases to avoid explosive mixtures), the reaction could be restarted within about 2 hours without cooling or draining the reactor by adding a catalyst in the +3 oxidation state (prepared as described in Example A) to the catalyst recycle stream and re-stabilising the reaction temperature.

It can be seen from Example 3 and Example B that a continous process can be maintained for a lengthy period provided that the percentage of cobalt in the +3 oxidation state in the recycled catalyst solution is maintained above 5%.

EXAMPLE C

The reaction vessel illustrated in FIG. 3 was charged with approximately 8 liters of a catalyst solution comprising 1.42% w/v cobalt, 10.7% of the cobalt being in the +3 oxidation state, in acetic acid containing ca. 8% water, recovered from the reaction products of a previous oxidation. The start-up procedure was essentially as described in Example 3 except that no additional catalyst solution was introduced. Oxidation of butane did not commence despite the attainment of a reaction temperature of ca. 150° C.

EXAMPLE 4

Example C was repeated except that 1.2 l/h of a catalyst solution comprising 0.91% w/v cobalt, of which about 12% was in the +3 oxidation state, dissolved in acetic acid containing approximately 6% w/w water was introduced. Butane oxidation commenced at 130° C within about 1½ hours after starting to introduce the catalyst solution containing a higher proportion of Co in the +3 oxidation state. Air and butane feed rates were then adjusted to maintain the desired rate of continuous oxidation.

EXAMPLE 5

The reaction vessel illustrated in FIG. 1 was started up with n-butane as feedstock in a manner similar to that described in Example 1. Continuous oxidation with "light ends" withdrawn as in Example 2 was maintained for some time thereafter.

A hydrocarbon feedstock comprising approximately 70% n-butane and 30% isobutane was then introduced together with a quantity of methyl ethyl ketone (MEK) approximately equal to the quantity of MEK withdrawn in the "light ends". Results obtained over a 12 hour 'balance' period are given in Table 4. It was found that the isobutane reaction at least as rapidly as the n-butane.

EXAMPLE 6

The reaction vessel illustrated in FIG. 1 was started up with n-butane as feedstock in a manner similar to that described in Example 1. Continuous oxidation with recycle of "light ends" as in Example 1 was maintained for some time thereafter (at a reaction pressure of ca. 35 bar gauge).

The n-butane feedstock was replaced with n-pentane of ca. 95% purity, the reaction temperature was adjusted to 140° C and the air feed rate to ca. 230 l./h (referred to S.T.P.). The liquid reaction product mixture contained ca. 1% cobalt, of which ca. 30% was in the Co(+3) oxidation state and the catalyst solution recovered and recycled from the low residence time distillation unit (illustrated in FIG. 2) still contained at least half this quantity of Co(+3). Continuous oxidation was sustained for 36 hours. Over a 12 hour period approximately 18.3 g/h pentane and 36.3 g/h oxygen were consumed to produce acetic acid (21.3 g/h), propionic acid (3.5 g/h), butyric acid (0.1 g/h), carbon monoxide (1.1 g/h) and carbon dioxide (17.1 g/h).

EXAMPLE 7 n-Hexane was then oxidised continuously at 130° C and a reaction pressure of ca. 35 bar gauge, in an essentially identical manner to that described in Example 6. Over a 12 hour period, approximately 22.7 g/h n-hexane and 21 g/h oxygen were consumed to give acetic acid (20.2 g/h), propionic (0.8 g/h), butyric acid (0.6 g/h), carbon monoxide (2.g/h) and carbon dioxide (12.3 g/h).

TABLE 1

|  | Example 1 "Light-ends" recycle | Example 2 "Light ends" withdrawal |
|---|---|---|
| Reaction Temperature (° C) | 110 | 110 |
| Reaction Pressure (bar) | 35 | 35 |
| Butane Feedrate (g/h) | 105–110 | 105–110 |
| Air Feedrate (l/h S.T.P.) | ca. 350 | ca. 350 |
| Cobalt concentration in catalyst solution returned through pipe 12 (% w/w) | ca. 1.0 | ca. 0.7 |
| Proportion as Co(+3) (%) | 30 | 40 |
| Oxygen consumption (g/h) | 70 | 64 |
| Acetic acid production (g/h) | 76 | 63 |
| Weight Selectivities | | |
| (g/100g butane consumed) | | |
| Acetic acid | 175 | 150 |
| Propionic Acid | 2 | <2 |
| Butyric acid | 1 | <2 |
| "Light ends" | — | 19 |
| "heavy ends" | <3 | <3 |

TABLE 1-continued

|  | Example 1 "Light-ends" recycle | Example 2 "Light ends" withdrawal |
|---|---|---|
| Carbon dioxide | 31 | 27 |
| Carbon Monoxide | 2 | 2 |
| Composition of "light ends" withdrawn (approx. % w/w) | | |
| Methyl ethyl ketone | | 70 |
| Sec-butyl acetate | | 20 |
| Ethyl acetate | | 5 |
| Methyl acetate | | 2.5 |
| Acetone | | 1.5 |

TABLE 2

|  | Feed to distill. Zone (Reaction Mixture) | Base Product (Catalyst Solution) | Distillate (Net Reaction Products) |
|---|---|---|---|
| Feedrate (g/h) | 300 | — | — |
| Take-off rate (g/h) | — | 210 | 90 |
| Compositions (% w/w) | | | |
| Water | 8.2 | 2.6 | 21 |
| Acetic Acid | 79.0 | 83.4 | 69 |
| Propionic Acid | 2.0 | 2.6 | 0.8 |
| Butyric acid | 3.7 | 4.5 | 0.5 |
| "Light ends"* | 2.6 | trace | 8.7 |
| "Involatiles"** | 4.4 | 6.6 | — |
| Cobalt concentration (% w/w) | 0.47 | 0.7 | — |
| Proportion as Co(+3) (%) | ca. 60 | ca. 40 | — |

*Composition of the "light ends" is given in Table 1.
**Involatiles comprise compounds of cobalt, together with "heavy ends" which consist in the main of succinic acid

TABLE 3

|  | Example 3 "Light-ends" Recycled |
|---|---|
| Reaction Temperature (° C) | 130.5 |
| Reaction Pressure (bar gauge) | 48.3 |
| Butane Feedrate (kg/h) | ca. 1.5 |
| Air Feedrate (m³/h at STP) | ca. 4.6 |
| Cobalt Concentration in Reactor Product (Butane Free) (% w/v) | 0.28 |
| Proportion as Co(+3) (%) | 26 |
| Cobalt Concentration in Recycled Catalyst Solution (% w/v) | 0.86 |
| Proportion as Co(+3) (%) | 10 |
| Oxygen Consumption Rate (Kg/h) | 1.15 |
| Acetic Acid Production Rate (kg/h) | 1.07 |
| Weight Selectivities | |
| (g/100 g butane consumed) | |
| Acetic Acid | 169 |
| Propionic Acid | 3 |
| Butyric Acid | 2 |
| Carbon Dioxide | 39 |
| Carbon Monoxide | 2 |

TABLE 4

|  | Example 5 Oxidation of n-butane/ isobutane Mixture |
|---|---|
| Reaction Temperature (° C) | 114 |
| Reaction Pressure (bar) | 35 |
| Hydrocarbon Feedrate (g/h) | 102 |
| MEK Feedrate (g/h) | 8 |
| Cobalt concentration in Recycled Catalyst Solution (% w/v) | 0.57 |
| Proportion as Co(+3) (%) | 37 |
| Conversion of n-Butane (%) | 28 |
| Conversion of Isobutane (%) | 33 |
| Oxygen Consumption (g/h) | 46 |
| Production Rate (g/h) of | |
| Acetic Acid | 33 |
| Propionic Acid | 0.5 |
| Butyric Acid | 0.4 |
| Carbon Dioxide | 12 |
| Carbon Monoxide | 1.5 |
| Acetone | 3.6 |
| t-Butanol | 6.7 |
| MEK | 8.6 |
|  | (i.e. 0.6 net) |

TABLE 4-continued

| | Example 5 Oxidation of n-butane/ isobutane Mixture |
|---|---|
| Ethyl Acetate | 0.8 |
| sec-Butyl Acetate | 1.8 |

We claim:

1. A process for the production of oxygen-containing organic compounds including a substantial proportion of acetic acid by the oxidation of a saturated aliphatic hydrocarbon containing from 3 to 7 carbon atoms or a mixture thereof which process consists of contacting the hydrocarbon or mixture thereof in a reaction zone with a molecular oxygen-containing gas in the presence of an essentially inert reaction medium and a soluble cobalt catalyst in an amount, calculated as cobalt, within the range from 0.1 to 10% by weight based on the weight of reaction medium, at a temperature in the range from 70 to 150° C and a pressure sufficient to maintain said reactants in the liquid phase, not less than 5 and not more than 90 percent of said cobalt catalyst being introduced into said reaction zone in the +3 oxidation state in a continuous process and not less than 11 and not more than 90% of said cobalt catalyst being introduced into said reaction zone in the +3 oxidation state in a batch process, to form a liquid product consisting of a mixture of oxygen-containing organic compounds containing a substantial proportion of acetic acid and water, feeding said liquid product to a distillation zone wherein a catalyst solution fraction consisting of inert reaction medium and cobalt, of which from 5 to 90 percent is in the +3 oxidation state for continuous operation and from 11 to 90% is in the +3 oxidation state for batch operation, is separated as a base product from a distillate fraction consisting of oxygen-containing organic compounds, the residence time of said catalyst solution in said distillation zone being so adjusted that it is the minimum consistent with substantially complete separation of said fractions so as to minimize the reduction of cobalt in the +3 oxidation state to cobalt in the +2 oxidation state to maintain the proportion of cobalt in the +3 oxidation state as hereinbefore defined, and thereafter recycling said catalyst solution to said oxidation zone.

2. A process according to claim 1 wherein said residence time of said catalyst solution in said distillation zone is less than 20 minutes when the separation of the fractions is carried out at atmospheric pressure.

3. A process according to claim 1 wherein said catalyst solution fraction or a part thereof is cooled and subjected to settling and/or filtration to remove "heavy ends" prior to recycle to said oxidation zone.

4. A process according to claim 1 wherein said saturated aliphatic hydrocarbon containing from 3 to 7 carbon atoms is n-butane.

5. A process according to claim 1 wherein said molecular oxygen-containing gas is air.

6. A process according to claim 1 wherein said inert reaction medium is a lower fatty acid containing from 2 to 4 carbon atoms.

7. A process according to claim 1 wherein said saturated aliphatic hydrocarbon containing from 3 to 7 carbon atoms is n-butane and said inert reaction medium is acetic acid.

8. A process according to claim 1 wherein said oxygen-containing organic compounds in the distillate fraction are separated by feeding said compounds to a first distillation column wherein a fraction comprising water, methyl ethyl ketone, sec-butyl acetate and minor amounts of alcohols and other volatile ketones and esters, is taken off as an overhead fraction and condensed, thereby forming a water-rich phase and a ketone/ester-rich phase, said water-rich phase being separated and returned wholly or partially to said first column at a point near the top thereof and said ketone/ester-rich phase being removed, passing said base product comprising acetic acid, water and carboxylic acid impurities to a second distillation column wherein water is removed overhead as an azeotrope leaving a base product comprising substantially anhydrous carboxylic acids and thereafter passing said base product from said second column to a third column wherein acetic acid is separated.

9. A process according to claim 8 wherein said ketone/ester-rich phase removed from said first column is recycled to said oxidation zone.

10. A process according to claim 1 wherein said oxygen-containing organic compounds in the distillate fraction are separated by feeding said compounds to a first distillation column wherein a fraction consisting of water, methyl ethyl ketone, sec-butyl acetate and minor amounts of alcohols and other volatile ketones is taken off as an overhead fraction and condensed, thereby forming a water-rich phase and a ketone/ester-rich phase, said water-rich phase being withdrawn and said ketone/ester-rich phase being returned at least in part to said column and a base product consisting of substantially anhydrous acetic acid and minor amounts of other carboxylic acids is removed and passed to a second distillation column wherein substantially pure acetic acid is separated from higher-boiling carboxylic acids.

* * * * *